United States Patent [19]

Mahurkar

[11] Patent Number: 5,221,256
[45] Date of Patent: Jun. 22, 1993

[54] MULTIPLE-LUMEN CATHETER

[76] Inventor: Sakharam D. Mahurkar, 6171 N. Sheridan Rd., #1112, Chicago, Ill. 60660

[21] Appl. No.: 833,311

[22] Filed: Feb. 10, 1992

[51] Int. Cl.$^5$ .......................................... A61M 25/00
[52] U.S. Cl. ........................................ 604/43; 604/280
[58] Field of Search ..................... 604/43, 280, 282; 128/4, 6

[56] References Cited

U.S. PATENT DOCUMENTS

| Re. 31,873 | 4/1985 | Howes . | |
|---|---|---|---|
| 2,173,527 | 9/1939 | Agayoff | 604/282 |
| 2,936,761 | 5/1960 | Snyder . | |
| 3,359,974 | 12/1967 | Khalil . | |
| 3,394,705 | 7/1968 | Abramson . | |
| 3,437,088 | 4/1969 | Bielinski . | |
| 3,593,713 | 7/1971 | Bogoff et al. . | |
| 3,726,281 | 4/1973 | Norton et al. . | |
| 3,995,623 | 12/1976 | Blake et al. . | |
| 4,004,588 | 1/1977 | Alexander . | |
| 4,016,879 | 4/1977 | Mellor . | |
| 4,057,065 | 11/1977 | Thow . | |
| 4,072,146 | 2/1978 | Howes . | |
| 4,100,246 | 7/1978 | Frisch . | |
| 4,168,703 | 9/1979 | Kenigsberg . | |
| 4,180,068 | 12/1979 | Jacobsen et al. . | |
| 4,180,076 | 12/1979 | Betancourt . | |
| 4,217,895 | 8/1980 | Sagae et al. . | |
| 4,257,416 | 3/1981 | Prager . | |
| 4,403,985 | 9/1983 | Boretos . | |
| 4,406,656 | 9/1983 | Hattler et al. . | |
| 4,484,585 | 11/1984 | Baier . | |
| 4,619,643 | 10/1986 | Bai | 604/43 |
| 4,692,141 | 9/1987 | Mahurkar | 604/43 |
| 4,701,159 | 10/1987 | Brown et al. . | |
| 4,753,640 | 6/1988 | Nichols et al. . | |
| 4,756,303 | 7/1988 | Kawashima et al. | 128/6 |
| 4,762,120 | 8/1988 | Hussein | 128/6 |
| 4,790,813 | 12/1988 | Kensey . | |
| 4,795,439 | 1/1989 | Guest | 604/43 |
| 4,813,429 | 3/1989 | Eshel et al. | 604/43 |
| 4,894,057 | 1/1990 | Howes . | |
| 4,898,591 | 2/1990 | Jang et al. | 604/232 |
| 4,934,340 | 6/1990 | Ebling et al. | 128/6 |
| 4,995,865 | 2/1991 | Gahara et al. . | |
| 5,004,455 | 4/1991 | Greenwood | 604/43 |
| 5,007,897 | 4/1991 | Kalb et al. | 604/43 |
| 5,015,232 | 5/1991 | Maglinte | 604/43 |
| 5,019,057 | 5/1991 | Truckai | 604/282 |
| 5,057,073 | 10/1991 | Martin | 604/43 |

FOREIGN PATENT DOCUMENTS 0322225  6/1989  European Pat. Off. .

OTHER PUBLICATIONS

*Dialysis & Transplantation* Arrow International, Inc. advertisement "Why Would Arrow Put a third lumen in a hemodialysis catheter?".

*Dialysis & Transplantation* Vas-cath Inc. advertisement "Vas-Cath introduces a new word in enhanced vascular access".

Mahurkar "The fluid mechanics of hemodialysis catheters", vol. XXXI *Trans. Am. Soc. Artif. Intern. Organs* 1985.

Hospital Price Schedule May 1988 for Arrow International Inc.

American Edwards Laboratories sales literature "EDSLAD Thermodilution and Monitoring Catheters".

American Edwards Laboratories sales literature "The EDSLAD 6F Thermodilution Catheter".

American Edwards Laboratories sales literature "EDSLAD 7F Thermodilution Catheter".

American Edwards Laboratories Thermodilution Catheter drawings.

*Primary Examiner*—Paul J. Hirsch
*Attorney, Agent, or Firm*—Arnold, White & Durkee

[57] ABSTRACT

A multiple-lumen catheter comprises an elongated cylindrical tube which has an internal diametral septum extending along the length thereof. This septum and the walls of the tube form at least three longitudinal lumens. The first and second lumens have substantially semi-circular transverse cross-sections which occupy the major portion of the transverse cross-section of the interior of the tube. A third lumen has a small transverse cross-section and is located at the intersection of one diametral end of the septum with the tube. This third lumen lies between a pair of adjacent corners of the first and second lumens.

58 Claims, 7 Drawing Sheets

MULTIPLE-LUMEN CATHETER

FIELD OF THE INVENTION

The present invention relates generally to multiple-lumen catheters for use in medical applications such as hemodialysis where fluids must flow simultaneously to and from a patient. This invention relates particularly to such catheters which have at least three lumens so that they can be used for hemodialysis of "critical care" patients who also require the injection of liquid medication, the withdrawal of blood samples for analysis, and/or the measurement of pressure in the vein to control the infusion rate of intravenous fluids so as to avoid fluid accumulation in the lungs and satisfy nutritional needs.

BACKGROUND OF THE INVENTION

Victims of trauma, burns, sepsis and other serious multi-system illnesses are managed in medical and surgical intensive care units. The incidence of acute renal failures in these settings is very high. Adequate dialysis treatment can be the only hope of survival for these patients.

Such "critical care" patients also need intravenous fluids at high rates, but the infusions must be carefully controlled in accordance with measurements of pressure in the vein to avoid fluid accumulation in the lungs. In addition, various medications, which are often incompatible when mixed together, need to be administered via different intravenous lines. Frequent sampling of blood is also required to assess the progress of the illness as well as the treatments being administered.

Critical care management can be carried out with a single-lumen catheter introduced in a central vein and used intermittently and sequentially for different functions, with some constraints. However, triple-lumen catheters such as those described in U.S. Pat. Nos. 3,995,623 to Blake; 4,406,656 to Hattler et al.; 4,072,146 (Re. 31,873) and 4,894,057 to Howes; 4,795,439 to Guest; and in European Patent Publication EP 0 440 992 A2 by Mahurkar, provide three independent dedicated lumens in a single catheter and opening at different sites in the vein. Such catheters permit simultaneous and continuous monitoring as well as treatment of all parameters, and are devices of choice in managing seriously ill patients. These triple-lumen critical-care catheters, however, are of little use for effective hemodialysis, because their inefficient flow geometry fails to provide a bidirectional blood flow of 250 ml per minute with a pressure gradient under 100 mm of mercury. Most of the time, therefore, a patient using a triple-lumen critical-care catheter also requires the insertion of an additional hemodialysis catheter in his central veins.

Hemodialysis is a process of mass transfer, in which certain chemical substances, accumulated in the blood because of kidney failure, are transferred from the blood across a semipermeable dialysis membrane to a balanced salt solution (dialysate). The quantity of the mass so transferred depends on its concentration in the blood and the volume of blood brought into contact with the dialysis membrane. The efficiency of a hemodialysis catheter, therefore, depends on the amount of a patient's blood that the catheter can deliver to the dialyzer each minute. Normally a hemodialysis catheter should deliver to the dialyzer about 250 millimeters of blood per minute under a pressure gradient of 100 millimeters of mercury, and return the same amount of dialyzed blood back to the patient under the same pressure gradient.

Early methods of dialysis access utilized two surgical cut downs for insertion of catheters, one in an artery and another in a vein. Later, two individual catheters were inserted in a single vein percutaneously (Shaldon's procedure). During the same period, McIntosh et al. described two single-lumen catheters of unequal length joined side by side and placed them in a femoral vein by surgical implantation. Uldall (Canadian patent 1,092,927) and Martin (Canadian patent 1,150,122) described two individual single-lumen catheters, arranged co-axially, one inside the other, for use in a subclavian vein for hemodialysis.

All these methods and devices are now essentially obsolete because of the need for two surgical insertion procedures for the single-lumen catheters, and the inefficient flow geometry of the co-axial catheters.

Efficient catheters incorporating semicircular flow geometry in parallel flow paths to provide high bidirectional blood flow rates, with axial separation of lumen ends to avoid admixture, are described in U.S. Pat. Nos. 4,134,402, Des. 272,651, 4,568,329, 4,692,141, 4,583,968, 4,770,652, 4,808,155, 4,842,582 and 4,895,561, and Canadian patent 1,193,508. These are the current dialysis access devices of choice. Their scientific basis is described in "Fluid Mechanics of Hemodialysis Catheters," *Transactions of American Society for Artificial Internal Organs*, Vol. XXXI, pp. 124–130 (1985).

Certain catheters have included a third, circular lumen located coaxially in the center of the internal septum of the dialysis catheter. This construction, however, compromises the efficiency of the other two lumens, and consequently such catheters do not meet the functional requirements for hemodialysis catheters as described in "Minimum Performance Standards for Double-Lumen Subclavian Cannulas for Hemodialysis," *Transactions of American Society for Artificial Internal Organs*, Vol. XXXII, pp. 500–502 (1986).

SUMMARY OF THE INVENTION

It is a primary object of this invention to provide an improved multiple-lumen catheter which has at least three lumens, two of which are capable of maintaining high fluid flow rates, such as the rates required in hemodialysis applications, and the third lumen does not significantly reduce the liquid throughput characteristics of the other two lumens, as compared with a catheter having only the first two lumens.

It is another important object of this invention to provide an improved multiple-lumen catheter which has two generally semi-cylindrical lumens suitable for use in hemodialysis, and a small third lumen positioned so that it does not have a significant adverse effect on the fluid flow characteristics of the two semi-cylindrical lumens.

A further object of this invention is to provide an improved multiple-lumen catheter which can be made of a soft elastic material such as silicone, with internal reinforcement to facilitate insertion of the catheter into a patient and to prevent collapse of the lumens during hemodialysis.

A still further object of the invention is to provide an improved multiple lumen catheter which resists kinking and buckling.

Still another object of the invention is to provide an improved triple-lumen catheter which avoids the need for an additional central venous catheter in a sick patient requiring hemodialysis, thereby eliminating the attendant risk of the surgical procedure required to place such an additional catheter in the patient.

A related object of this invention is to preserve the peripheral veins of a patient for construction of arteriovenous fistula used for chronic maintenance dialysis, by avoiding the trauma of repeated punctures, thrombosis and possible infection of peripheral veins when used for blood sampling and intravenous infusions.

Yet another object of this invention is to provide an improved triple-lumen catheter in which the third lumen can be used to contain a removable stylus which provides the column strength needed to facilitate insertion of the catheter over a flexible Seldinger guide wire without buckling or kinking. The third lumen can also be used for removal of a blocked catheter from a patient's vein over a guide wire inserted through the third lumen.

Other objects and advantages of the invention will become apparent from the following detailed description and the accompanying drawings.

In accordance with the present invention, the foregoing objectives are realized by providing a multiple-lumen catheter comprising an elongated cylindrical tube having an internal diametral septum extending along the length thereof, the septum and the walls of the tube forming at least three longitudinal lumens, two of the lumens having substantially semi-circular transverse cross-sections occupying the major portion of the transverse cross section of the interior of the tube, and the third lumen having a small transverse cross-section and located at the intersection of one diametral end of the septum with the tube, between a pair of adjacent corners of the two semi-circular lumens.

DESCRIPTION OF THE PREFERRED EMBODIMENTS

While the invention is susceptible to various modifications and alternative forms, specific embodiments thereof have been shown by way of example in the drawings and will herein be described in detail. It should be understood, however, that it is not intended to limit the invention to the particular forms disclosed, but, on the contrary, the intention is to cover all modifications, equivalents and alternatives falling within the spirit and scope of the invention as defined by the appended claims.

Turning now to the drawings and referring first to FIGS. 1-9, there is shown a triple-lumen hemodialysis catheter 10 which is a modification of the catheter described in Mahurkar U.S. Pat. No. 4,583,968, issued Apr. 22, 1986, for "Smooth Bore Double Lumen Catheter". This catheter 10 has an elongated cylindrical body portion 11 made of polyurethane. The body portion 11 is hollow except for a longitudinal, diametral septum 12 which divides the interior of the hollow cylinder into three parallel lumens 13, 14 and 15.

The major portion of the transverse width of the septum or divider 12 is in the form of a flat strip which divides the interior of the cylinder 11 into two large lumens 13 and 14 having generally semi-circular transverse cross-sections. At one diametral end, the septum 12 is bifurcated to form the smaller third lumen 15. It will be understood that the major portion of the septum need not be perfectly flat, but could have a minor degree of curvature or other geometric configuration.

In the preferred embodiment, the two larger lumens 13 and 14 are substantially semii-cylindrical with generally D-shaped cross sections (FIG. 2) which occupy the major portion of the transverse cross-section of the interior of the cylindrical tube. As illustrated by the arrows in FIGS. 3 and 4, the lumen 13 is the blood-intake lumen, and the lumen 14 is the blood-return lumen.

The smaller third lumen 15 is located at one diametral end of the septum 12, where the septum is bifurcated before it joins the cylindrical outer wall of the catheter. Thus, the lumen 15 is located between two adjacent corners of the generally D-shaped lumens 13 and 14. This third lumen 15 has a circular transverse cross-section and can be used for a variety of different purposes, such as injecting liquid medications into the patient, withdrawing blood samples from the patient, or measuring the pressure in the vein of the patient. Because the lumen 15 is located at the corners of the lumens 13 and 14, there is only a slight reduction in the liquid-handling capacity of the lumens 13 and 14. For example, the lumens 13 and 14 are still capable of delivering 250 ml/min. of blood with a pressure gradient of 100 mm. of mercury, as required in most dialysis systems. A small lumen located in the corners of the large lumens 13 and 14 does not significantly reduce the liquid flow rates in the large lumens because the corners are regions where boundary layers of zero or low velocity converge and form a stagnation zone. A small lumen located in these corners is well away from the regions of high fluid flow in the lumens 13 and 14.

Because the third lumen provided by this invention does not significantly compromise the blood flow rates in the two large lumens, a single catheter may be used for both hemodialysis and to provide access to the central veins of the patient for intravenous infusions, withdrawal of blood samples, and monitoring of venous pressures. This preserves the peripheral veins of the patient for construction of arterio-venous fistula, which are used for chronic maintenance hemodialysis. The third lumen also may be used for other purposes, such as for containing a removable stylus to add column strength during insertion of the catheter, or to receive a guide wire for use in replacing a blocked catheter.

Figures 1, 2, 3, 5:
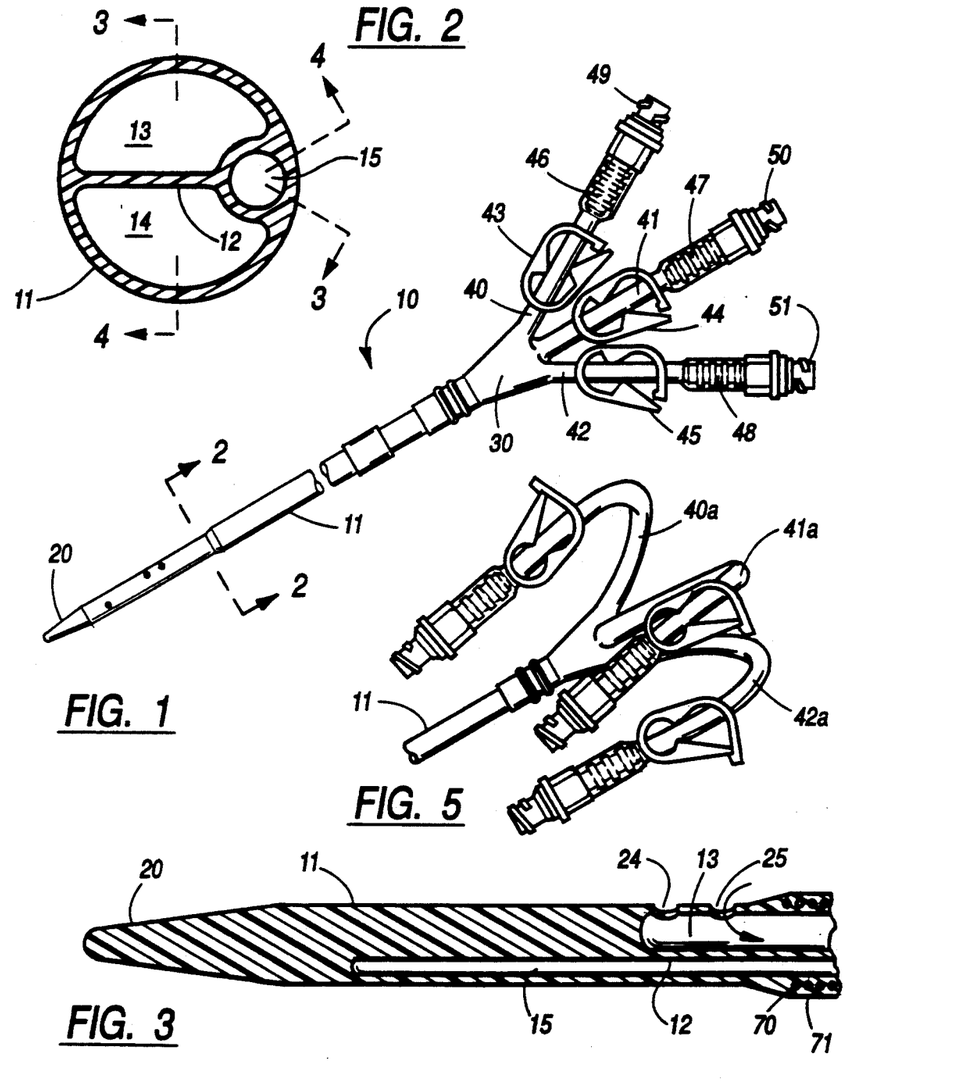
FIG. 1 is a perspective view of a triple-lumen catheter assembly embodying the present invention.
FIG. 2 is an enlarged section taken generally along line 2—2 in FIG. 1.
FIG. 3 is a section taken generally along time 3—3 in FIG. 2.
FIG. 5 is a perspective view of the same catheter shown in FIG. 1, with a modified connecting system attached to its proximal end.
Figure 4:
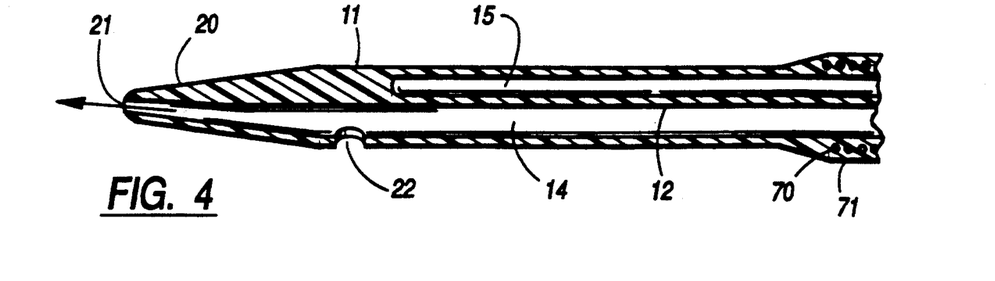
FIG. 4 is a section taken generally along line 4—4 in FIG. 2.
Figures 6, 7, 8, 9:
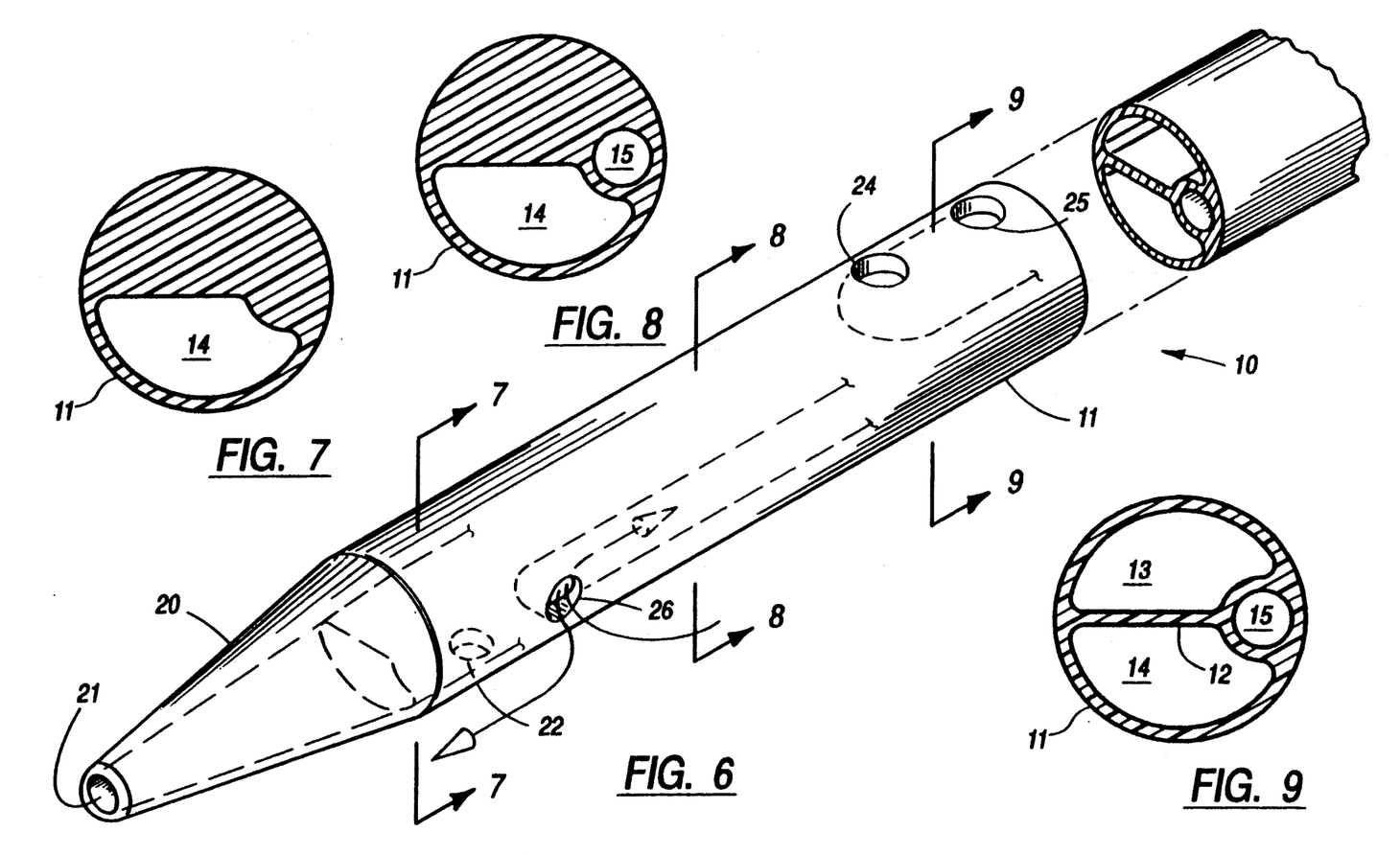
FIG. 6 is an enlarged perspective view of the distal portion of the catheter of FIG. 1, with a portion broken away to show the internal structure.
FIG. 7 is an enlarged section taken generally along line 7—7 in FIG. 6.
FIG. 8 is an enlarged section taken generally along line 8—8 in FIG. 6.
FIG. 9 is an enlarged section taken generally along line 9—9 in FIG. 6.

At the distal end of the catheter, the exterior surface of the cylinder 11 merges into a smoothly tapered frusto-conical tip 20. On the inside, the blood return lumen 14 extends longitudinally all the way through the tip 20, bending slightly as it passes through the tip so that it opens at 21 near the center of the distal end of the conical tip, as can be seen in FIGS. 3 and 4. Within the tip 20, the cross-sectional shape of the lumen 14 gradually changes from generally D-shaped at the proximal end of the tip 20 (see FIG. 6) to circular at the distal end of the tip (see FIG. 6). The transition from D to circular is illustrated by the broken lines in FIG. 6.

The catheter tip 20 may be molded as a unitary part of the catheter tube. This is accomplished by placing a tip mold around the distal end of an extruded tube which forms the three lumens, with a mold insert in place for forming the extension of the return lumen 14 through the tip. Plugs of thermoplastic material are preferably inserted in the distal ends of the lumen before forming the tip by thermo-forming or radio-frequency energy.

In addition to the opening 21 at the distal end of the blood-return lumen 14, an auxiliary aperture 22 is formed in the side wall of the lumen 14. The side aperture 22, which is spaced longitudinally away from the distal opening 21 toward the proximal end of the catheter, ensures the flow of blood through the return lumen 14 even in situations where the distal opening 21 might become wholly or partially blocked. The area of the apertures 21 and 22 is preferably at least equal to the transverse cross-sectional area of the return lumen 14.

In order to provide a longitudinal spacing between the distal openings of the two lumens 13 and 14, the blood-intake lumen 13 is terminated at an aperture 24 in the side wall of the catheter, spaced longitudinally away from the aperture 22. An auxiliary aperture 25 spaced longitudinally from the aperture 24 permits blood to enter the lumen 13 freely without excessive vacuum in the event of a blockage of the aperture 24 against the wall of the vein into which the catheter 10 is inserted.

The small third lumen 15 terminates at an aperture 26 in the sidewall of the catheter. This aperture 26 is located approximately midway between the apertures 21 and 24 in the longitudinal direction, and 90° away from the aperture 24 in the circumferential direction. The aperture 26 is also spaced proximally away from the aperture 22 in the longitudinal direction. Thus, liquids injected into a patient through the lumen 15 are injected downstream of the blood intake ports 24 and 25, and blood samples withdrawn through the lumen 15 are taken upstream of the ports 21 and 22 where purified blood is returned to the patient.

At the proximal end of the catheter 10, the three lumens 13-15 open into a diversion means in the form of Y-shaped connector or hub 30 (FIG. 1) which forms three internal passageways communicating with the proximal ends of the catheter lumens. The proximal ends of the catheter lumens are preferably expanded slightly to fit over mating sections at the distal end of the hub 30, with the inside walls of the catheter lumens being bonded to the mating walls of the hub 30 by solvent or ultrasonic bonding. The distal ends of the hub passageways have the same cross-sectional shapes and dimensions as the respective expanded lumens 13-15 so that they form extensions of the catheter lumens. Alternatively, the hub may be molded in place on the end of the catheter, using mold inserts to form the hub passageways. The hub passageways diverge from each other as they extend toward the proximal end of the hub, and they also increase in cross-sectional area.

To facilitate connection of the catheter hub 30 to the conventional tubes leading to a dialysis unit, injection syringes, or other extracorporeal equipment, and also to accommodate clamps for opening and closing the fluid passageways, the hub 30 forms extension tubes 40, 41 and 42 (FIG. 1). These extension tubes 40–42 are long enough to receive conventional clamps 43, 44 and 45 for opening and closing the respective tubes. The extension tubes are relatively soft and flexible, so that they can be easily manipulated and also easily closed by the pressure of the clamps 43–45. The clamps 43 and 44 serve as on-off valves for controlling the flow of blood between the catheter and the dialysis unit. The proximal ends of the tubes 40–42 receive respective ferrules 46, 47 and 48 formed as integral parts of luer connectors 49, 50 and 51. The luer connectors serve as coupling means for coupling the proximal ends of the extension tubes to the flexible tubes leading to the extracorporeal equipment.

FIG. 5 illustrates modified extension tubes 40a, 41a and 43a which are generally U-shaped, as described in Mahurkar U.S. Pat. No. 4,895,561. The bent portions of the extension tubes have a memory so that they assume the desired U shape when not under the influence of an external force. As described in that patent, the U-shaped bends in the extension tubes enable the auxiliary connecting elements attached to the proximal end of the catheter to be accommodated in a small area around the access site on the patient's body. Furthermore, any pulling forces exerted on the extension tubes by the relatively heavy tubes leading to the dialysis unit tend to push the catheter into the patient to hold it in place, rather than accidentally withdrawing the catheter. Consequently, the risk of accidental dislodgement of the catheter is greatly reduced, as is the risk of vein irritation and damage.

In the modified embodiment of FIGs. 10-13, the catheter body is formed of silicone, which requires thicker walls because it is a soft elastic material. Silicone is preferred for certain applications because it is inert and is tolerated by the human body for long periods of time without reaction. To compensate for the pliability of the silicone, a reinforcing strip 60 is embedded in the septum 12, extending along the full length of the intake lumen 13 and beyond the distal end of that lumen. The reinforcing strip 60 is made of a material which is substantially stiffer than the silicone used to form the main body of the catheter, so that the catheter can be advanced against a resistance by the application of force proximally of the resistance. The reinforcing strip 60 also prevents collapse of the lumens when the pressure differential of a dialysis system exists across the septum. The reinforcing strip 60 is inserted longitudinally within a hollow septum 12 formed by two transversely spaced diametral webs 12a and 12b which are integral parts of the catheter body. If desired, the strip 60 may be co-extruded with the tube which forms the catheter body.

The reinforcing strip 60 is made of a material that is stiff enough to transmit longitudinally applied forces to the conical tip 20 at the distal end of the catheter so that the catheter can be readily inserted into a patient percutaneously, i.e., without surgical intervention. One suitable material for the reinforcing strip is nylon, which provides the requisite degree of stiffness in a strip 0.012 inch thick.

With the reinforcing strip 60, a silicone catheter can be easily inserted through a peel-apart sheath. Such a sheath is typically used after a guide wire has been introduced into a patient's vein by use of an access needle. The puncture formed by the needle is subsequently dilated by a smooth plastic tip on the end of a dilator telescoped through the pull-apart sheath and inserted a short distance into the patient's vein. The dilator is then removed, the catheter is inserted through the sheath, and finally the sheath is removed by stripping it apart along two longitudinal tear lines.

Without the reinforcing strip 60, attempts to insert a silicone catheter by the technique described above may result in buckling or radial expansion of the catheter at the entry to the sheath, due to the frictional resistance of the silicone surface engaging the inside wall of the sheath. Rather than causing the catheter to slide through the sheath, the applied insertion force may result in buckling or expansion of the soft, elastic silicone material of the catheter body against the proximal end of the sheath, thereby preventing the catheter from sliding through the sheath.

With the reinforcing strip, however, the longitudinal pushing is transmitted by the reinforcing member to the tip of the catheter, thereby "pulling" the catheter through the sheath. That is, the relatively stiff reinforcing member provides the catheter with sufficient column strength for easy insertion through the sheath. Although presently available materials that have the stiffness needed in the reinforcing material are not suitable for long-term implantation in the human body because of incompatibility problems such as localized allergic reactions, the structure of FIGS. 10-13 enables the reinforcing material to be isolated from the body. That is, the nylon reinforcing material is surrounded by the silicone material of the hollow septum. Therefore, it is only the silicone material that comes into contact with internal body tissues or fluids.

The reinforcing strip 60 also prevents collapse of one of the lumens due to the pressure differential that normally exists across the septum of a dual-lumen catheter while it is being used to withdraw blood under a negative pressure in one lumen and to return blood under a positive pressure in the other lumen. With a silicone catheter, it is possible for the septum and the outside wall of the negative-pressure lumen to collapse together, thereby closing that lumen. The reinforcing strip 60, however, provides sufficient rigidity to the septum to prevent the negative-pressure lumen from collapsing. Even when the outer wall of the lumen is not reinforced, the curvature of that wall normally prevents it from being collapsed against the septum as long as the septum itself cannot be distorted substantially toward the outer wall.

To prevent acute bends in the catheter from closing off one or both lumens, the catheter of FIGS. 10-13 has a spiral 70 of relatively stiff material embedded in the cylindrical wall of the catheter along a substantial portion of the length of the catheter. The spiral 70 is preferably a thin metal wire wound helically around the extruded silicone tube, and then covered with a layer 71 of silicone so that the wire is not exposed to body tissues. The silicone is preferably applied as a liquid so that it flows around the spiral 70 and becomes a part of the silicone side walls of the catheter. If desired, a strong polymeric monofilament, e.g., nylon, may be used instead of the metal wire. The spiral 70 will always tend to retain its cylindrical shape, and thus also tends to hold the outer wall of the catheter in a cylindrical shape, thereby resisting kinking or buckling of the catheter side walls. Consequently, the catheter can be bent, even at acute angles, without closing the lumens.

Figures 10, 11, 12, 13:
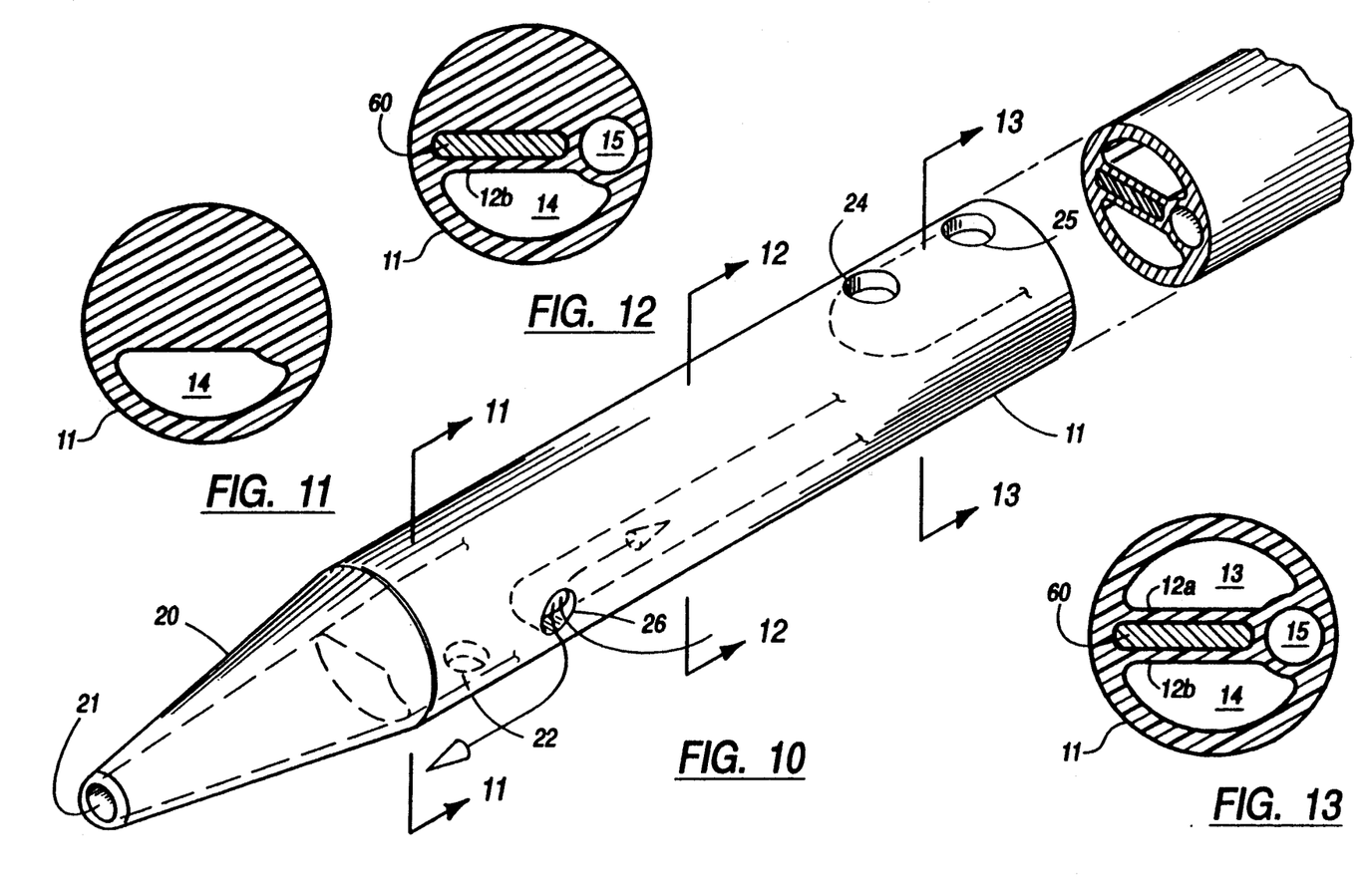
FIG. 10 is an enlarged perspective of the distal portion of a modified catheter design embodying the invention.
FIG. 11 is an enlarged section taken generally along line 11—11 in FIG. 10.
FIG. 12 is an enlarged section taken generally along line 12—12 in FIG. 10.
FIG. 13 is an enlarged section taken generally along line 13—13 in FIG. 10.
Figures 14, 15, 16, 17:
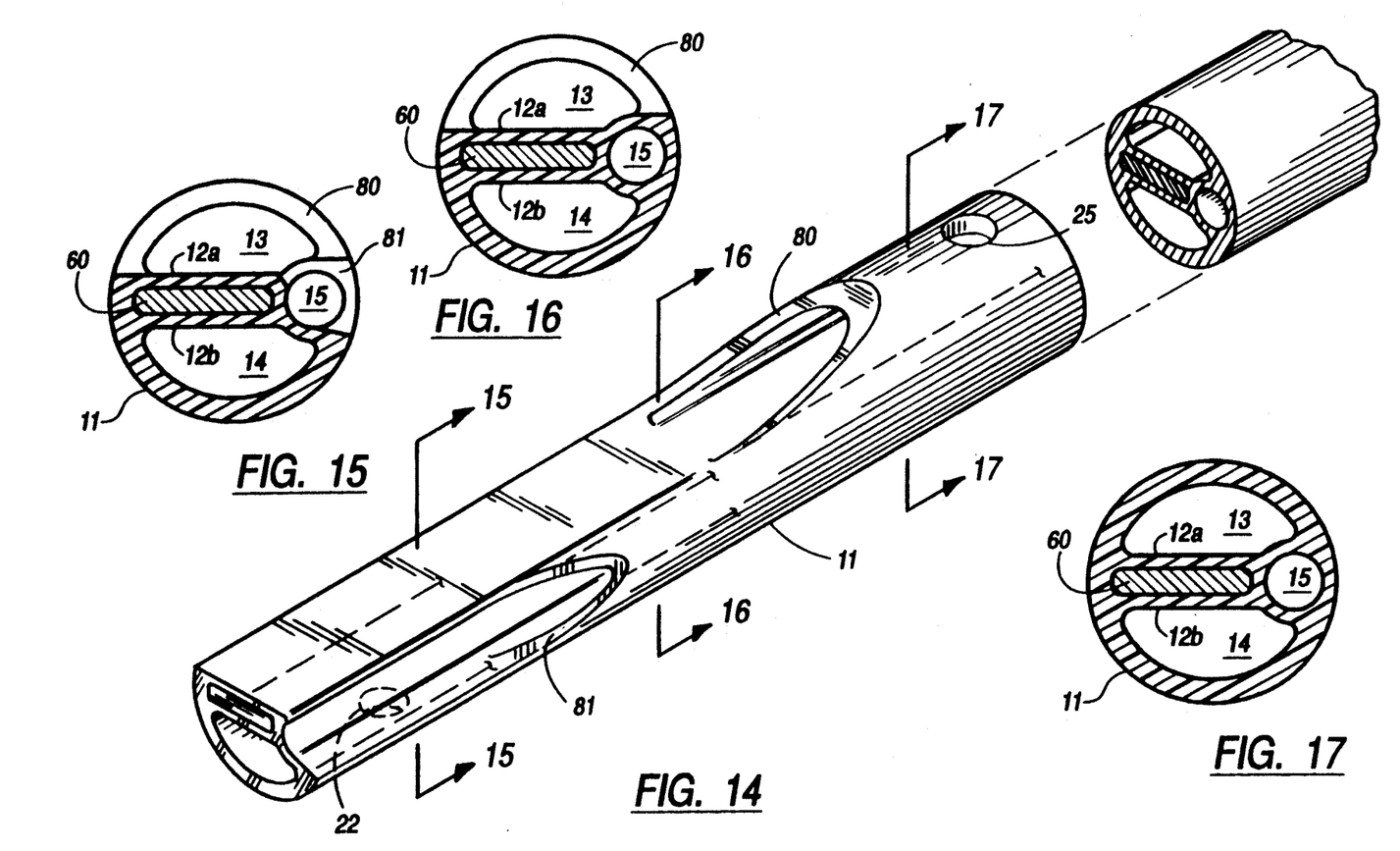
FIG. 14 is an enlarged perspective of the distal portion of another modified catheter embodying the invention.
FIG. 15 is an enlarged section taken generally along line 15—15 in FIG. 14.
FIG. 16 is an enlarged section taken generally along line 16—16 in FIG. 14.
FIG. 17 is an enlarged section taken generally along line 17—17 in FIG. 14.
Figures 18, 19, 20, 21:
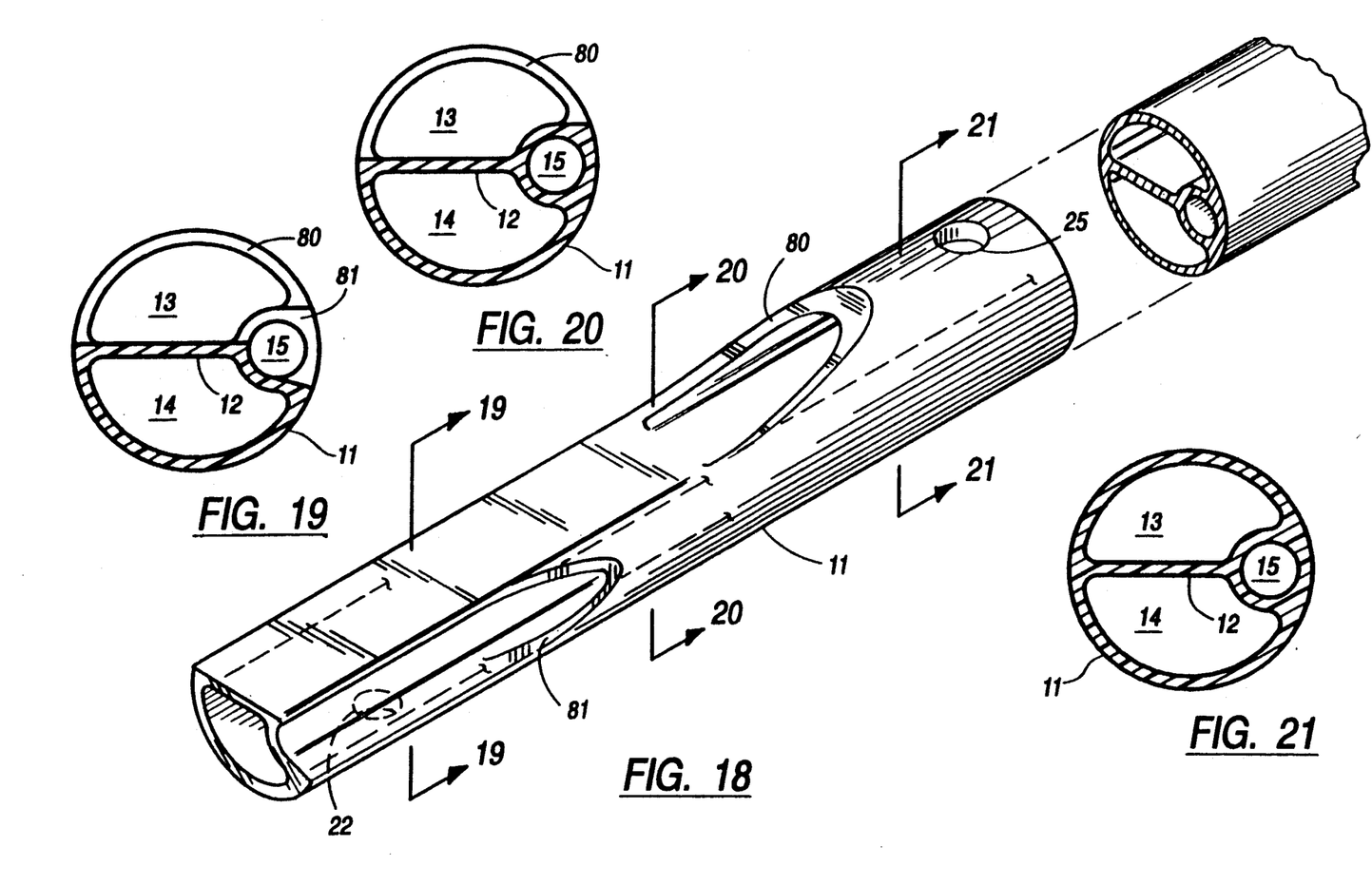
FIG. 18 is an enlarged perspective view of the distal portion of a modified catheter design embodying the invention.
FIG. 19 is an enlarged section taken generally along line 18—18 in FIG. 18.
FIG. 20 is an enlarged section taken generally along line 20—20 in FIG. 18.
FIG. 21 is an enlarged section taken generally along line 21—21 in FIG. 18.
Figures 22, 23, 24, 25:
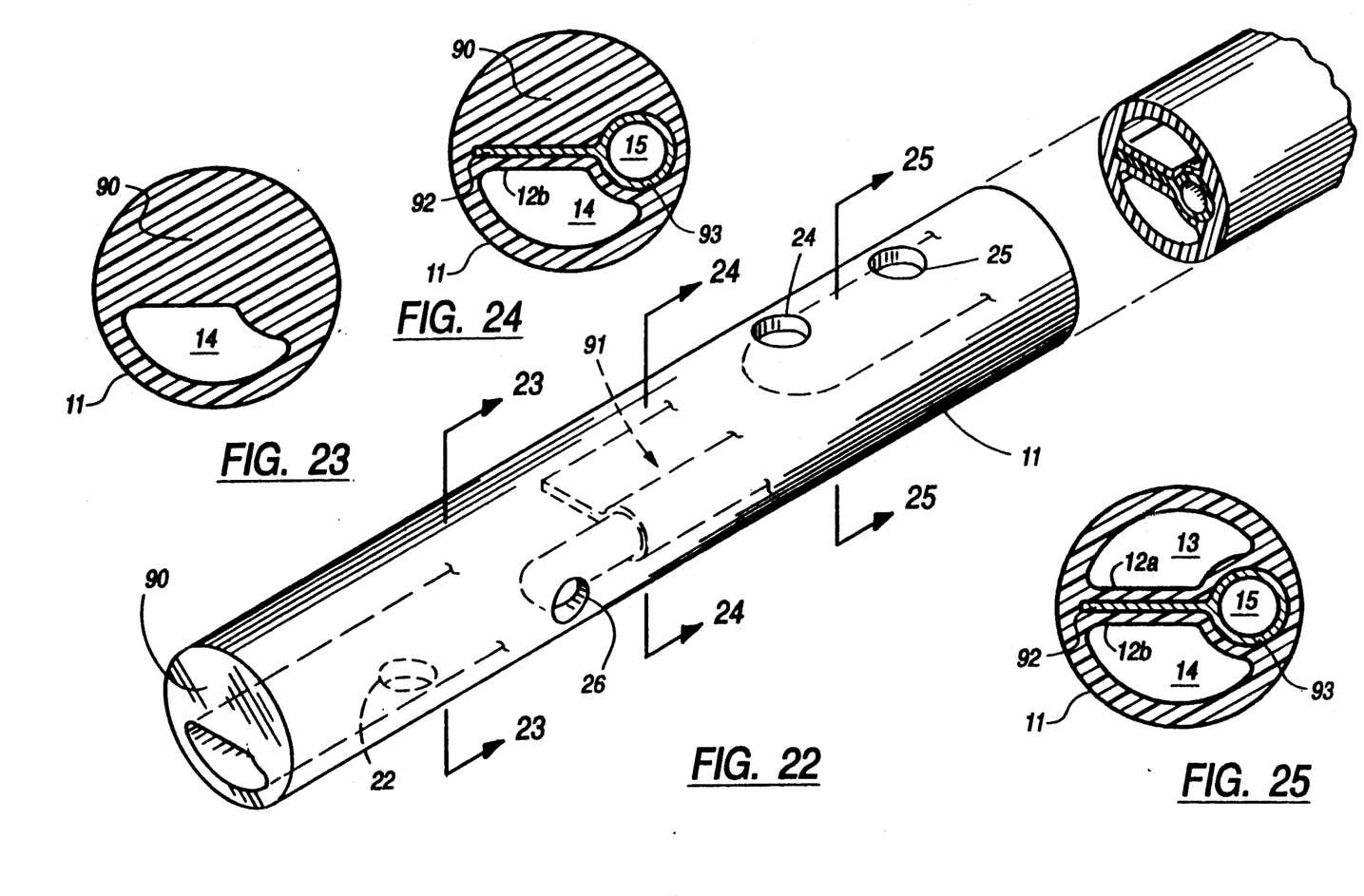
FIG. 22 is an enlarged perspective of the distal portion of a modified catheter design embodying the invention.
FIG. 23 is an enlarged section taken generally along line 23—23 in FIG. 22.
FIG. 24 is an enlarged section taken generally along line 24—24 in FIG. 22.
FIG. 25 is an enlarged section taken generally along line 25—25 in FIG. 22.
Figures 26, 27, 28, 29:
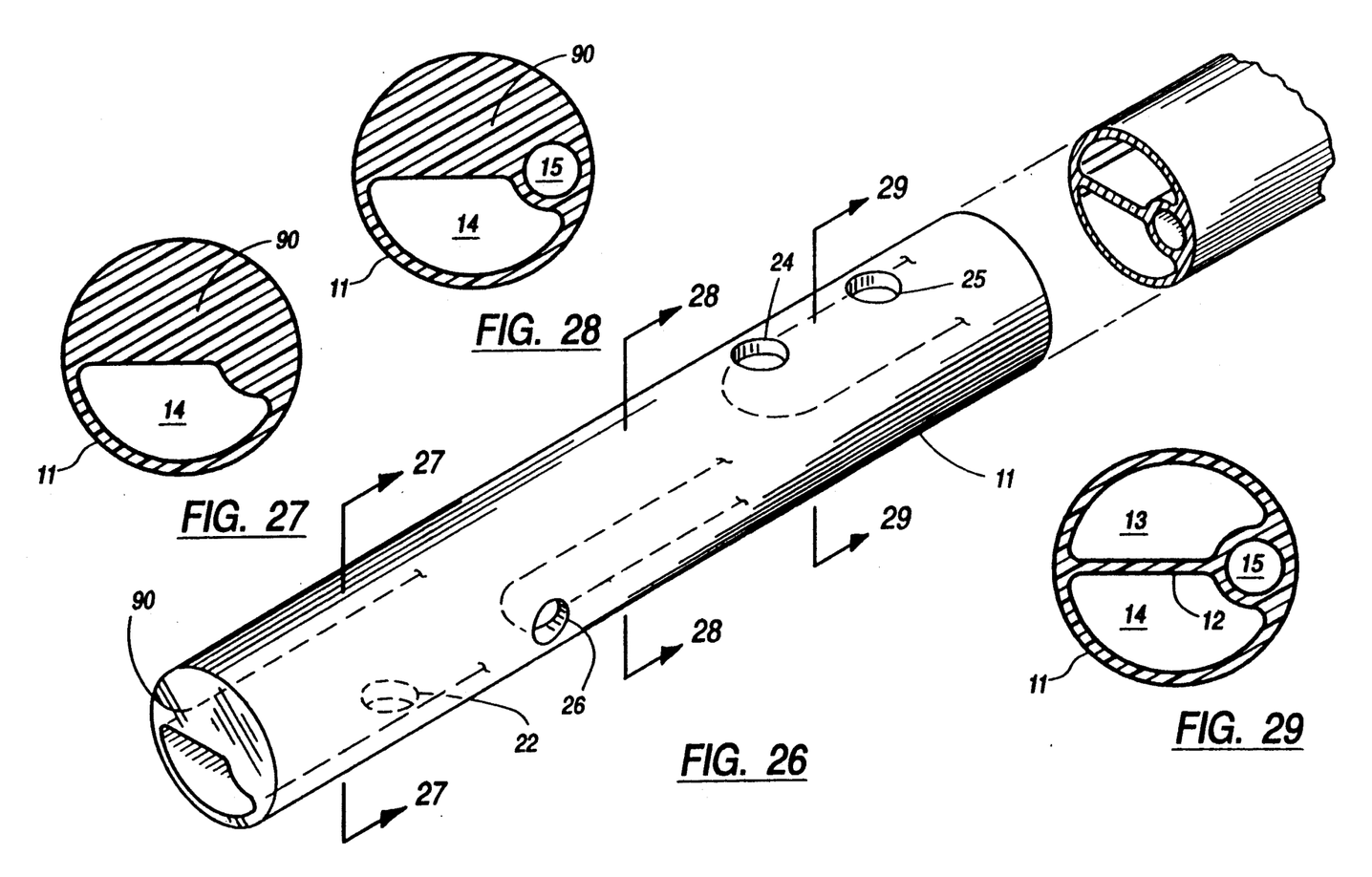
FIG. 26 is an enlarged perspective of the distal portion of another modified catheter embodying the invention.
FIG. 27 is an enlarged section taken generally along line 27—27 in FIG. 26.
FIG. 28 is an enlarged section taken generally along line 28—28 in FIG. 26.
FIG. 29 is an enlarged section taken generally along line 29—29 in FIG. 26.

The preferred method of making the catheter of FIGS. 10-13 is to extrude the main body portion of the catheter as a cylindrical tube having a hollow septum for receiving the reinforcing strip 60 (see FIG. 10). The extruded tube can be cut into the desired lengths for individual catheters. The strip 60 is then inserted into the central cavity, and the tip 20 and the hub 30 are formed on opposite ends of the tube by conventional techniques. Alternatively, the dual-lumen tube can be co-extruded with a continuous reinforcing strip in the septum.

The end portion of the reinforcing strip 60 may be provided with a plurality of holes so that molten silicone will flow through the holes in the reinforcing strip. Then when the silicone is subsequently solidified, the reinforcing strip is locked firmly to the catheter by the material that solidifies within the holes of the strip. This interlocking of the reinforcing strip and the silicone holds the reinforcing strip securely in place, and ensures that the strip does not penetrate or separate through the relatively soft silicone tip during and after the insertion of the catheter.

At the proximal end of the catheter, the reinforcing strip 60 may be similarly interlocked with the material that forms the hub 30. Thus, the proximal end of the strip 60 may form one or more holes for receiving molten polymer during the in-situ molding of the hub 30. Then when the polymer solidifies, the strip 60 is securely interlocked within the hub 30.

FIGS. 14-29 illustrate different configurations for the distal ends of catheters embodying this invention. Thus, in the catheters of FIGS. 14-21, the intake lumen 13 and the small lumen 15 are terminated with open ends 80 and 81 by simply slicing off distal portions of the lumen with beveled cuts. The return lumen 14 continues all the way to the distal end of the tube, and retains the same generally D-shaped cross sectional configuration along its entire length, or it may be made with a cylindrical configuration. The catheter of FIGS. 14-17 is formed with a silicone body and a nylon reinforcing strip 60, while the catheter of FIGS. 18-21 is formed with a polyurethane body and thus has thinner walls.

In the catheters of FIGS. 22-29, the intake lumen 13 and the small lumen 15 are terminated by a solid portion 90 which extends from the distal end of the tube to the edges of the sidewall apertures 24 and 26. The return lumen 14 is exactly the same as in the catheters of FIGS. 14-21 described above. The catheter of FIGS. 22-25 is formed with a silicone body and nylon reinforcing member 91 which includes both a flat strip 92 and a narrow hollow cylinder 93. The strip 92 is located between the webs 12a and 12b, and the cylinder 93 lines the inside walls of the small lumen 15. This lumen is not used to conduct blood except for withdrawal of samples for analysis, and is normally closed when it is not being used for intravenous infusions or pressure monitoring. Thus, exposure of the nylon reinforcing material on the inside walls of the lumen 15 will not normally cause the patient's body to react to the catheter during prolonged implacements of the catheter. The reinforcing member 91 may be co-extruded with the silicone body of the catheter, or it may be formed separately and then inserted into the silicone body.

I claim:

1. A multiple-lumen catheter comprising
an elongated cylindrical tube having an internal diametral septum extending along the length thereof, said septum and the walls of said tube forming at least three longitudinal lumens, first and second of said lumens having substantially semi-circular transverse cross-sections occupying the major portion of the transverse cross section of the interior of said tube, and a third lumen having a small transverse cross-section and located at the intersection of one diametral end of said septum with said tube, between a pair of adjacent corners of said first and second lumens.

2. The multiple-lumen catheter of claim 1 wherein a major portion of the transverse width of said septum is flat so that said first and second lumens have generally D-shaped cross sections.

3. The multiple-lumen catheter of claim 1 which includes a hollow conical tip on the distal end of said tube, the outside surface of said conical tip merging smoothly with the outside surface of said tube, and the inside surface of said conical tip merging smoothly with the inside surface of one of said first and second lumens, the distal ends of the other lumens being longitudinally spaced from the distal end of said tip and from each other.

4. The multiple-lumen catheter of claim 3 wherein said conical tip forms a solid connection from the distal ends of said other lumens to the distal end of said tip.

5. The multiple-lumen catheter of claim 1 wherein said third lumen has a circular transverse cross-section.

6. The multiple-lumen catheter of claim 1 wherein said first lumen extends all the way through the distal end of said tube, said second lumen terminates at an aperture spaced longitudinally from the distal end of said tube, and said third lumen terminates at an aperture located longitudinally between the distal end of said tube and the termination of said second lumen.

7. The multiple-lumen catheter of claim 1 wherein said elongated cylindrical tube is made of a soft, elastic material, and which includes a reinforcing member embedded within said elastic material and extending along the length of said tube, said reinforcing member being made of a material which is substantially stiffer than the material of said tube so that the catheter can be advanced against a resistance by the application of force proximally of the resistance and so that said first and second lumens will not collapse when pressure differential of a dialysis system exists across said septum.

8. The dual-lumen catheter of claim 7 wherein said septum comprises a pair of transversely spaced diametral webs formed as integral parts of said tube, and said reinforcing member comprises a flat strip of stiff material inserted longitudinally between said webs and bonded thereto.

9. The dual-lumen catheter of claim 7 wherein said reinforcing member is made of nylon.

10. A multiple-lumen catheter comprising
an elongated generally cylindrical body, and
a septum extending diametrically across the interior of said body and along the length thereof to divide said interior into at least three longitudinal lumens,
a major portion of the diametral width of said septum comprising a flat strip which forms two substantially semi-cylindrical, longitudinal lumens on opposite sides thereof,
one transverse end of said septum being bifurcated and cooperating with the contiguous portion of the side wall of said body to form a small longitudinal lumen between adjacent corners of said semi-cylindrical lumens.

11. The multiple-lumen catheter of claim 10 wherein the portions of said small lumen on opposite sides of the central plane of said septum are symmetrical with respect to that plane.

12. A multiple-lumen catheter comprising
a unitary elongated flexible tube having a circular transverse cross-section and an internal diametral divider extending along the length thereof to divide the interior of said tube into identical first and second lumens having generally semi-circular transverse cross sections, and a third lumen formed by a bifurcation at one diametral end of said divider and the adjoining portion of the tube side wall, said third lumen having a generally circular transverse cross-section, the distal ends of said first, second and third lumens being longitudinally spaced from each other,
diversion means attached to the proximal end of said catheter and forming three separate fluid passageways each of which is in fluid communication with one of said lumens, and three extension tubes attached to the proximal end of said diversion means, each of said tubes being in fluid communication with one of said passageways.

13. The multiple-lumen catheter of claim 12 wherein the distal opening of said first lumen is at the distal end of said tube, and the distal openings of said second and third lumens are in the side walls of said tube.

14. The multiple-lumen catheter of claim 12 wherein the distal end of said tube forms a frusto-conical tapered tip that smoothly merges with the circumference of said tube.

15. The multiple-lumen catheter of claim 14 wherein one of said generally semi-circular lumens extends through said tip and forms a distal opening at the apex of said tip.

16. The multiple-lumen catheter of claim 12 wherein each of said generally semi-circular lumens has an auxiliary opening in the side wall of said tube and spaced from the distal opening of that.

17. The multiple-lumen catheter of claim 12 wherein each of said extension tubes is bent back toward the distal end of the catheter.

18. The multiple-lumen catheter of claim 17 wherein the bent portions of said extension tubes have a memory so that they assume a predetermined shape when not under the influence of an external force.

19. The multiple-lumen catheter of claim 12 which includes a reinforcing member enclosed within said divider and having a stiffness greater than that of said tube.

20. The multiple-lumen catheter of claim 19 wherein said reinforcing member surrounds the side walls of said circular lumen.

21. The multiple-lumen catheter of claim 12 wherein the distal portion of said tube, beyond the distal end of the shorter semi-circular lumen, is cylindrical.

22. A multiple-lumen catheter comprising
a first elongated tube having proximal and distal ends and a substantially circular transverse cross-section,
a second elongated tube having a substantially circular transverse cross-section and a smaller diameter than the radius of said first tube and extending along an inside wall of said first tube and joined thereto,
an internal divider extending from said second tube across the remainder of the interior of said first tube, said divider extending along a diameter of said first tube and a projected diameter of said second tube,
the combination of said first and second tubes and said divider forming a pair of longitudinal lumens of generally semi-circular transverse cross-section on opposite sides of said divider, and a smaller third longitudinal lumen of circular transverse cross-section defined by said second tube, the distal ends of the three lumens being longitudinally spaced from each other, and the proximal ends of all three lumens being located at the proximal end of said tube.

23. The multiple-lumen catheter of claim 22 wherein the distal opening of said first lumen is at the distal end of said tube, and the distal openings of said second and third lumens are in the side walls of said tube.

24. The multiple-lumen catheter of claim 22 wherein the distal end of said tube forms a frusto-conical tapered tip that smoothly merges with the circumference of said tube.

25. The multiple-lumen catheter catheter of claim 24 wherein one of said generally semi-circular lumens extends through said tip and forms a distal opening at the apex of said tip.

26. The multiple-lumen catheter of claim 22 wherein each of said generally semi-circular lumens has an auxiliary opening in the side wall of said tube and spaced from the distal opening of that.

27. The multiple-lumen catheter of claim 22 wherein each of said extension tubes is bent back toward the distal end of the catheter.

28. The multiple-lumen catheter of claim 27 wherein the bent portions of said extension tubes have a memory so that they assume a predetermined shape when not under the influence of an external force.

29. The multiple-lumen catheter of claim 22 which includes a reinforcing member enclosed within said divider and having a stiffness greater than that of said tube.

30. The multiple-lumen catheter of claim 29 wherein said reinforcing member surrounds the side walls of said circular lumen.

31. The multiple-lumen catheter of claim 22 wherein the distal portion of said tube, beyond the distal end of the shorter semi-circular lumen, is cylindrical.

32. A multiple-lumen catheter comprising
an elongated cylindrical tube having an internal diametral septum extending along the length thereof,
the side wall of said tube extending inwardly to form a small longitudinal lumen along one side of the interior of the tube, said small lumen having a circular transverse cross section and extending from the proximal end of said tube to a distal opening which is spaced from the distal end of said tube, the remainder of the interior of said tube forming two lumens having distal openings which are longitudinally spaced from each other and from the distal opening of said small lumen.

33. A triple-lumen hemodialysis catheter consisting of
a first elongated, unitary, flexible, cylindrical tube having a side wall which forms an integral, co-tangential second tube forming a generally circular lumen that has a diameter smaller than the radius of the first tube, and
an axial, integral, internal, flat divider separating the interior of said first tube into second and third elongated lumens each of which has a transverse cross section that is generally D-shaped with a dented corner,
all three of said lumens having separate openings at the distal end thereof so that the three lumens are in independent fluid communication with the interior of a vein,
said second lumen extending beyond the distal opening of the said first lumen to the end of the said first tube while said third lumen ends on a circumferential opening that is axially spaced from the end of said first tube,
the proximal end of the said first tube having means to diverge said three lumens from each other and communicating them with respective extension tubes having female luer ends.

34. The catheter of claim 33 which has a frusto-conical tapered tip that smoothly merges with the circumference of the said first tube.

35. The catheter of claim 34 wherein said second lumen extends through and exits at the apex of the said frusto-conical tapered tip.

36. The catheter of claim 33 wherein each of said first and third lumens has at least one additional aperture proximal to its distal opening.

37. The catheter of claim 33 which includes extension tubes each of which assumes a curved 180° bent shape when not under the influence of an external force.

38. The catheter of claim 33 which includes an elongated strip of reinforcing material enclosed within said internal divider.

39. The catheter of claim 33 wherein the portion of the catheter beyond the distal opening of said third lumen is cylindrical.

40. The catheter of claim 33 wherein the distal portion of said third lumen is removed.

41. A unitary elongated flexible tube having a circular transverse cross section and containing an eccentric, codiametral, tangential lumen of generally circular cross-section with a diameter smaller than the radius of said tube, and a diametral divider that divides the remainder of the tube into two identical, substantially semicircular lumens, the proximal ends of all the said lumens communicating via diversion means with respective extension tubes, the distal ends of all the said lumens being open to communicate with the interior of a vein, one of the semicircular lumens extending to the end of the tube and the other semicircular lumen opening on its own circumference proximal to the end of the tube, the smaller circular lumen opening by a circumferential aperture intermediate the distal openings of the two semicircular lumens, the distal end of the said catheter being adapted for insertion into a vein.

42. The catheter of claim 41 which has a frusto-conical tapered tip that smoothly merges with the circumference of the said first tube.

43. The catheter of claim 42 wherein one of said semicircular lumens extends through and exits at the apex of the said frusto-conical tapered tip.

44. The catheter of claim 41 wherein the other semicircular lumen and said circular lumen each has at least one additional aperture proximal to its distal opening.

45. The catheter of claim 41 which includes extension tubes each of which assumes a curved 180° bent shape when not under the influence of an external force.

46. The catheter of claim 41 which includes an elongated strip of reinforcing material enclosed within said diametral divider.

47. The catheter of claim 41 wherein the portion of the catheter beyond the distal opening of said other semicircular lumen is cylindrical.

48. The catheter of claim 41, wherein the distal portion of said other semicircular lumen is removed.

49. A multilumen catheter comprising a flexible elongated tube, having proximal and distal ends, the tube enclosing in its interior, a smaller circular tube in circumferential contact with the main tube and having a common diametral plane with said main tube and an axial septum contacting the exterior of the smaller circular tube and interior of the catheter, said septum extending in the said common diametral plane to form two independent longitudinal substantially semicircular lumens which are larger than the lumen formed by said smaller circular tube, the first larger lumen extending to and opening at the distal end of the tube, and the second larger lumen opening proximally of the distal end of the tube on the surface of the catheter, the smaller circular lumen communicating with the exterior of the catheter intermediate the distal openings of said first and said second lumens, the proximal ends of each lumen being connected to and communicating with respective extension tubes via flow diversion means, the distal end of the catheter being adapted for insertion into a vein.

50. The catheter of claim 49 which has a frusto-conical tapered tip that smoothly merges with the circumference of the tube.

51. The catheter of claim 50 wherein one of said semicircular lumens extends through and exits at the apex of said frusto-conical tapered tip.

52. The catheter of claim 51 wherein the other semicircular lumen and said circular lumen each has at least one additional aperture proximal to its distal opening.

53. The catheter of claim 49 which includes extension tubes each of which curves toward the tip of the catheter.

54. The catheter of claim 53 wherein said extension tubes assume a curved 180° bent shape when not under the influence of an external force.

55. The catheter of claim 49 which includes an elongated strip of reinforcing material enclosed within said diametral septum.

56. The catheter of claim 52 wherein the portion of the catheter beyond the distal opening of said other semicircular lumen is cylindrical.

57. The catheter of claim 52 wherein the distal portion of said other semicircular lumen is removed.

58. The catheter of claim 52 wherein the distal portion of said other semicircular lumen is blocked off beyond its distal opening.

* * * * *